United States Patent [19]

Kesling, Jr.

[11] 4,222,959

[45] Sep. 16, 1980

[54] PROCESS FOR THE PREPARATION OF AROMATIC FORMAMIDES

[75] Inventor: Haven S. Kesling, Jr., Drexel Hill, Pa.

[73] Assignee: Atlantic Richfield Company, Los Angeles, Calif.

[21] Appl. No.: 46,089

[22] Filed: Jun. 6, 1979

Related U.S. Application Data

[63] Continuation-in-part of Ser. No. 961,816, Nov. 17, 1978, abandoned, which is a continuation of Ser. No. 754,152, Dec. 27, 1976, abandoned.

[51] Int. Cl.$^3$ .................. C07C 102/00; C07C 103/34
[52] U.S. Cl. ........................... 260/562 R; 260/561 R
[58] Field of Search ...................... 260/562 R, 561 R

[56] References Cited

U.S. PATENT DOCUMENTS

| | | | |
|---|---|---|---|
| 2,793,211 | 5/1957 | LoCicero | 260/562 R |
| 3,099,689 | 7/1963 | Cragg | 260/562 R |
| 3,530,182 | 9/1970 | Haines | 260/561 R |

FOREIGN PATENT DOCUMENTS 1244550 9/1960 France.
4426447 6/1966 Japan.

OTHER PUBLICATIONS

Beckwith, The Chemistry of Amides, Interscience Publishers N.Y., N.Y., 1970, p. 118.
Saegusa et al., Tet. Letters, 1966, #49, pp. 6125-6129.
Saegusa et al., Bull. Chem. Soc., Japan, 42 (1969), pp. 2610-2614.
Nefedov et al., Izv. Akad. Nauk., SSUR, Ser Khim, #7, (1973), pp. 1536-1540.

*Primary Examiner*—Arthur P. Demers
*Attorney, Agent, or Firm*—Coleman R. Reap

[57] ABSTRACT

A process for the preparation of aromatic formamides by reacting an aromatic amine with carbon monoxide in the presence of a solvent, a catalytic quantity of a copper salt and oxygen, or an oxygen-containing gaseous mixture. The reaction is preferably carried out in the presence of excess amine, a volatile alcohol solvent, and a copper halide catalyst.

15 Claims, No Drawings

PROCESS FOR THE PREPARATION OF AROMATIC FORMAMIDES

RELATED APPLICATIONS

This is a Continuation-in-part application of U.S. patent application Ser. No. 961,816 filed Nov. 17, 1978, now abandoned, which in turn is a continuation application of U.S. patent application Ser. No. 754,152 filed Dec. 27, 1976, now abandoned.

BACKGROUND OF THE INVENTION

This invention relates to the preparation of formamides and more particularly to the preparation of aromatic formamides by the reaction of aromatic amines with carbon monoxide.

Formamides are valuable as industrial solvents and as starting materials for the preparation of important chemical intermediates and finished chemicals, such as isocyanates. Increasing interest in formamides has led to investigations for more economical and efficient processes for their production. Much recent research has been directed to the preparation of formamides by the carbonylation reaction between amines and carbon monoxide using various metal catalysts. Unfortunately, these reactions have been generally catalyzed by expensive Group VIII noble metal catalysts, such as the salts of palladium and platinum. Some success has been observed in the carbonylation of aliphatic and heterocyclic amines to formamides with carbon monoxide using relatively inexpensive copper salts, however, these catalysts were found not to be effective in catalyzing the reaction of aromatic amines with carbon monoxide to produce aromatic formamides (U.S. Pat. No. 2,677,706; T. Saegusa et al, Tetrahedron Letters, Vol. 49, pp 6125–6129 (1966); T. Saegusa et al, Bull. Chem. Soc. Japan, Vol. 42, pp 2610–2614 (1969); B. Nefedov et al, Izv. Akad. Nauk. S.S.S.R. Ser Khim, No. 7, pp 1536–1540, July 1973). Since carbon monoxide is a very inexpensive starting material and copper salts are relatively inexpensive catalysts, the preparation of formamides from amines and carbon monoxide using copper salt catalysts is potentially of considerable economic importance. Accordingly, it would be desirable to adapt this procedure to the preparation of aromatic formamides from aromatic amines.

SUMMARY OF THE INVENTION

The above-described process has been improved by this invention so that aromatic formamides can now be prepared by the reaction of carbon monoxide with aromatic amines using copper salts as catalysts. Accordingly, it is an object of the invention to present an improved method for the preparation of formamides. It is another object of the invention to present a new method for preparing aromatic formamides. It is another object of the invention to present a method for preparing aromatic formamides by the reaction of carbon monoxide with aromatic amines. It is another object of the invention to present a method of preparing aromatic formamides using copper salts as catalysts. It is another object of the invention to present a method for producing aromatic formamides in high yields by the reaction of aromatic amines with carbon monoxide using copper salt catalysts. It is another object of the invention to present a method of preparing aromatic formamides from aromatic amines and carbon monoxide using a regenerating cooper catalyst system. These and other objects of the invention will become more obvious from the following description and examples.

The above objects are achieved by carbonylating aromatic amines with carbon monoxide in the presence of an organic solvent and a small amount of oxygen or an oxygen-containing gas mixture using a copper salt catalyst. The reaction is generally carried out at a temperature in the range of about 60° to 300° C. and a pressure of about 1 to 700 atmospheres. In preferred embodiments the copper salt is a copper halide, the organic solvent is a lower aliphatic alcohol, the reaction zone temperature is in the range of about 100° to 250° C., the reaction zone pressure is in the range of about 50 to 150 atmospheres, a dehydrating agent is present in the reaction zone, the reaction is carried out in the presence of excess amine and the amount of oxygen present in the reaction zone is less than the lower limit of the explosive range of mixtures of oxygen and carbon monoxide.

DESCRIPTION OF THE INVENTION

The carbonylation reaction of the invention may be carried out in any high pressure batch-type or continuous reactor. A general procedure is to charge the amine, catalyst, and the oxygen or oxygen-containing gas mixture into the reaction vessel, introduce the proper amount of carbon monoxide gas to obtain the desired reaction pressure and then heat the mixture to and maintain it at the desired temperature for the appropriate period. The reaction can be carried out batchwise or as a continuous process and the order of addition of the reactants to the reaction vessel may be varied as desired. The reaction products can be conveniently recovered by any conventional method such as filtration, distillation, etc. to effect separation of the formamide from unreacted materials, catalyst, byproducts, etc.

Any monofunctional or polyfunctional primary, secondary or tertiary aromatic amine or mixture of aromatic amines may be used in the process of the invention. The amine reactant has the structural formula $$R(NR_1R_2)_n$$

wherein R is an aromatic group comprised of 1 to 3 condensed or non-condensed rings, $R_1$ is hydrogen, a saturated or unsaturated aliphatic organic group containing up to 30 carbon atoms or an aromatic group comprised of 1 to 3 condensed rings, $R_2$ is hydrogen or a saturated or unsaturated aliphatic group containing up to 30 carbon atoms and n is at least 1.

R may be unsubstituted or substituted with one or more alkyl groups containing up to 12 carbon atoms each, or other substituents such as halide, hydroxy, ether, ester, mercaptan, thioether, thioester, amino, amido, nitro, nitroso, etc., substituents or organic groups containing these substituents.

When $R_1$ is an aliphatic organic group it can be a hydrocarbon or it can contain one or more of the substituents enumerated above as being optionally present in R. $R_1$ is preferably hydrogen or an alkyl group having up to 12 carbon atoms. When $R_1$ is an aromatic group it can be any of the groups mentioned in defining R and it may be the same as or different from R.

When $R_2$ is an aliphatic organic group it can be any of the groups encompassed in defining $R_1$ and it can be the same as or different from $R_1$. $R_2$ is also preferably hydrogen or an alkyl group having up to 12 carbon atoms.

When n is 1 the amine is polyfunctional. Preferred amines are those in which n is 1 to 3.

If it is desired, a mixture of two or more aromatic amines can be used as the amine reactant. Also, the reaction mixture can contain one or more aliphatic or heterocyclic amines in addition to the aromatic amine reactant.

Representative aromatic amines include aniline, N-methylaniline, N,N-dimethylaniline, N-methyl-N-ethylaniline, the toluidines, N-methyl-o-toluidine, N,N-dimethyl toluidine, the xylidines, N-methyl-N-ethyl-xylidine, N-methyl-p-hexylaniline, N-heptyl-m-pentylaniline, chloroaniline, N-methyl-p-bromoaniline, nitroaniline, nitrosoaniline, cyanoaniline, methoxyaniline, N-pentyl-o-nitroaniline, p-hydroxyethylaniline, N,N-dimethyl-m-mercaptopropylaniline, the phenylene diamines, the toluene diamines, N,N-diphenylamine, N-propyl-N-toluidinylaniline, 4,4'-diaminodiphenylmethane, $\alpha$-napthylamine, $\beta$-naphthylamine, etc. The preferred aromatic amines are the mononuclear aromatic amines, such as aniline, N-methylaniline, N,N-dimethyl aniline, phenylene diamine, etc.

The copper salts usable as catalysts in the process of the invention include copper(I) and copper(II) salts and mixtures of these. In general, any copper salt usable as a catalyst can be used in the invention. The copper salt anions may be inorganic, such as the halides, sulfates, sulfites, nitrates, nitrites, carbonates, etc.; or organic, such as acyl groups, including acetate, formate, propionate, alkoxides such as methoxide, ethoxide, etc.

Examples of representative copper salts are copper(I) chloride, copper(II) chloride, copper(II) bromide, copper(II) fluoride, copper(II) formate, copper(II) acetate, copper(I) propionate, copper(II) methoxide, copper(I) ethoxide, etc. The preferred copper salts are the halides, particularly the copper(II) halides, such as copper(II) chloride and copper(II) bromide.

The amount of catalyst used in the reaction may vary from the minimum amount which is catalytically effective up to about 15%, based on the total weight of aromatic amine present in the reaction zone. Amounts greater than about 15% can be used, if desired, however, the efficiency of the reaction decreases as larger amounts of catalyst are employed. The amount of copper salt catalyst usually used in the process of the invention varies from about 0.01 to about 15%, and preferably from about 0.1 to about 5%, based on the total weight of aromatic amine present in the reaction zone.

A ligand or coordination complex compound of the metal catalyst can be included, if desired, in the catalyst formulation to modify the properties of the copper salt catalyst. Examples of suitable compounds include organic ligands, such as alkyl or aryl phosphines, arsines or stibines and inorganic ligands, such as tin chloride, etc. When these agents are included they are often used in amounts up to about four molar equivalents of ligand per mole of copper.

The reaction is carried out in the presence of a catalyst oxidizing agent. During the reaction between the carbon monoxide and the aromatic amine, the copper(II) ions are reduced to copper(I) ions. The oxidizing agent functions to oxidize the copper back to the copper(II) state. It is not known what additional part the oxidizing agent plays in the process of the invention, but it has been discovered that aromatic amines will not react with carbon monoxide to produce aromatic formamides in the absence of an oxidizing agent, such as oxygen. Suitable oxidizing agents include oxygen or other suitable oxidizing agents, such as quinone. When oxygen is used it may be introduced as pure oxygen or as a component in a gas mixture, such as air. The amount of oxygen present in the reaction zone at any given time is preferably such that the concentration of oxygen is less than 6.1 volume percent. This is the lower limit of the explosive range of oxygen in carbon monoxide. Although the reaction can be carried out at oxygen levels of 6.1 volume percent or greater, it is preferred to keep the oxygen and carbon monoxide levels at safe concentrations to avoid the hazard of an explosion.

The reaction can be carried out with or without the use of a solvent, however, it is preferred to use a solvent. The preferred solvents are organic polar solvents especially the lower aliphatic or cycloaliphatic alcohols, i.e., those containing up to 8 carbon atoms, because they are easily separated from the product by evaporation or distillation. The most preferred solvents are the saturated aliphatic alcohols having up to 6 carbon atoms. Typical lower aliphatic and cycloaliphatic alcohols include methanol, ethanol, the propanols, the butanols, the hexanols, cyclohexanol, etc. The amount of alcohol solvent in the reaction zone is not critical, but it is usually preferred to use a sufficient quantity to completely dissolve the reactants and to prevent localized overheating. The optimum amounts for each reaction system can be easily determined.

Some of the alcohol may react with the aromatic amine and carbon monoxide to produce aromatic urethanes. The amount of aromatic urethane side product can be minimized by carrying out the reaction in the presence of a stoichiometric excess of amine. The excess amine, which serves to increase the basicity of the reaction mixture, may be the aromatic amine used as the principal reactant or it may be any other aromatic amine or any aliphatic or heterocyclic amine, such as pyridine, etc. that will not compete with the aromatic amine undergoing reaction. The equivalent ratio of total amine to alcohol is usually about 2:1 to 10:1 and preferably about 2:1 to 4:1.

During the course of the reoxidation of the copper(I) salt back to a copper(II) salt, water is produced. Since water tends to poison the catalyst and causes other side reactions, it is preferred to carry out the reaction under conditions such that the water formed during the reaction process is removed from the reaction zone. This can be accomplished by process techniques, such as azeotropic distillation or by carrying out the reaction in the presence of a dehydrating agent. When azeotropic distillation is employed the water can be removed with a portion of the solvent. Suitable azeotropic mixtures are those formed between alcohols and water. The use of dehydrating agents is often preferable to the use of azeotropic distillation. The dehydrating agent can be efficiently used at concentrations ranging up to about 50%, based on the total weight of aromatic amine used. When a dehydrating agent is used it is preferably used at concentrations of about 25 to 50%, based on the total weight of aromatic amine present in the reaction zone. Suitable dehydrating agents include organic drying agents such as orthoesters, ketals, acetals, enolethers, trialkylorthoborates, and various inorganic drying agents, such as molecular sieves and calcium chloride. Preferred dehydrating agents are those which will release lower alcohols, i.e., aliphatic or cycloaliphatic alcohols having up to 8 carbon atoms in their structures, upon reaction with water. Examples of preferred dehydrating agents are trimethylorthoformate, triethylorthoformate, tributylorthoformate, 2,2-dimethyoxypropane, 2,2-di-n-butoxypropane, 1,1-dimethoxycyclohexane, 1,1-di-n-butoxycyclohexane, 1,1-dimethoxymethane, 1,1-diethoxyethane, 2-ethoxyprop-2-ene, 1-methoxycyclohex-1-ene, trimethylborate. Particularly preferred dehydrating agents are the orthoesters which, when hydrolyzed with water, release alcohols having up to 6 carbon atoms in their structures. It is most preferred that the alcohol being released be the alcohol which is used as reaction solvent.

The following examples illustrate specific embodiments of the invention. Unless otherwise indicated, parts and percentages are in a weight basis.

EXAMPLE I

A solution of 23.28 g (250 mmoles) of aniline, 19.78 g (250 mmoles) of pyridine, 53.06 g (500 mmoles) of trimethylorthoformate, and 60.00 g of absolute methanol is charged into a 300 ml stainless steel stirred autoclave, along with 3.36 g (25 mmoles) anhydrous copper-(II) chloride. The autoclave is sealed and charged with carbon monoxide to a pressure of 1500 psig. The temperature in the autoclave is raised to and maintained at 150° C. Reaction is initiated by charging oxygen into the autoclave until the pressure reaches 1600 psig. The gas charge line is then flushed by charging carbon monoxide into the reactor until the autoclave pressure reaches 1700 psig. A strong exotherm and a rapid pressure drop of about 950 psi over the course of a 120 minute residence period is observed. GLC (gas-liquid chromatograph) and ALC (analytical liquid chromatograph) analyses indicate that 4.83 g (39.9 mmoles) of formanilide is formed. Based on aniline as the limiting reagent, a selectivity of 30.2 mole % at 52.8% aniline conversion is obtained.

EXAMPLE II

The procedure of Example I is repeated except that 12.65 g (125 mmoles) of triethylamine is substituted for the pyridine and a mixture of 4.12 g (25 mmoles) of anhydrous copper(II) sulfate and 0.55 g (2.8 mmoles) of anhydrous copper(I) iodide is substituted for the copper(II) chloride. A strong exotherm and a rapid pressure drop of about 1125 psi over the course of a 180 minute residence period is observed. GLC and ALC analyses indicate that 12.56 g (103.7 mmoles) formanilide is formed. Based on aniline as the limiting reagent, a selectivity of 49.3 mole % formanilide at 84.1% aniline conversion is obtained.

EXAMPLE III

The procedure of Example I is repeated except that 30.28 g (250 mmoles) N-methylaniline is substituted for the aniline. GLC and ALC analyses will indicate the formation of N-methylformaniline.

EXAMPLE IV

The procedure of Example II is repeated except that 26.75 g (250 mmoles) of N-methylaniline is substituted for the aniline and a mixture of 4.12 g (25 mmoles) of anhydrous copper(II) sulfate and 0.55 g (2.8 mmoles) of anhydrous copper(I) iodide is substituted for the copper(II) chloride. A strong exotherm and a rapid pressure drop of about 200 psi over the course of a 15 minute period is observed. The oxygen-carbon monoxide addition cycle is repeated three more times in increments of 100 psi each over the course of a 120 minute residence period. A total pressure drop of 1250 psi is observed. GLC and ALC analyses indicate the presence of 16.62 g (123.1 mmoles) of N-methylformanilide. Based on N-methylaniline as the limiting reagent, a selectivity of 52.3 mole % to N-methylformanilide at 94.3% N-methylaniline conversion is obtained.

EXAMPLE V

The procedure of Example I is repeated except that 35.79 g (250 mmoles) of anhydrous copper(II) sulfate and 0.55 g (2.8 mmoles) of anhydrous copper(I) iodide is substituted for the copper(II) chloride. GLC and ALC analyses will indicate the presence of N-2-naphthylformamide.

EXAMPLE VI

The procedure of Example I is repeated except that no pyridine is added to the reaction formulation. GLC and ALC analyses will indicate the formation of formanilide.

EXAMPLE VII

The procedure of Example I is repeated except that no trimethylorthoformate is added to the reaction formulation. GLC and ALC analyses will indicate the formation of formanilide.

EXAMPLE VIII

The procedure of Example I is repeated except that the methanol is replaced with methyl acetate. GLC and ALC analyses will indicate the formation of substantial amounts of formanilide.

Although the invention has been described with particular reference to specific examples, it is understood that the scope of the invention is not limited thereto but is only determined by the breadth of the appended claims.

I claim:

1. A process for the preparation of aromatic formamides which comprises reacting an aromatic amine having the structural formula $$R(NR_1R_2)_n$$

wherein R is an aromatic group comprised of 1 to 3 condensed or non-condensed rings, $R_1$ is hydrogen, a saturated or unsaturated aliphatic organic group containing up to 30 carbon atoms or an aromatic group comprised of 1 to 3 condensed rings, $R_2$ is hydrogen or a saturated or unsaturated aliphatic group containing up to 30 carbon atoms and n is at least 1 with carbon monoxide at a temperature of about 60° to 300° C. and a pressure of about 1 to 700 atmospheres in the presence of a sufficient amount of a copper compound catalyst to effect the carbonylation of the aromatic amine, an agent capable of oxidizing copper and a dehydrating agent present in an amount sufficient to remove water formed during said reaction.

2. The process of claim 1 wherein the copper compound is present in an amount of about 0.01 to 15% based on the total weight of aromatic amine present.

3. The process of claim 2 wherein the copper compound is an inorganic salt.

4. The process of claim 3 wherein the copper salt is a copper halide.

5. The process of claim 4 wherein the copper halide is present in an amount of about 0.1 to 5% based on the total weight of aromatic amine present.

6. The process of claim 1 wherein the copper compound is an organic salt.

7. The process of claim 1 wherein the copper oxidizing agent is oxygen.

8. The process of claim 7 wherein the oxygen concentration in the reaction zone is less than the minimum amount which will form an explosive mixture of carbon monoxide and oxygen.

9. The process of claim 1 wherein the dehydrating agent is a member of the group consisting of orthoesters, ketals, acetals, enolethers, trialkylorthoborates, and mixtures of these.

10. The process of claim 1 wherein an organic polar solvent is present in the reaction zone.

11. The process of claim 10 wherein said organic polar solvent is an aliphatic or cycloaliphatic alcohol containing up to 8 carbon atoms.

12. A process for the preparation of aromatic formamides which comprises reaction an aromatic amine having the structural formula $$R(NR_1R_2)_n$$

wherein R is an aromatic group comprised of 1 to 3 condensed or non-condensed rings, $R_1$ is hydrogen, a saturated or unsaturated aliphatic organic group containing up to 30 carbon atoms or an aromatic group comprised of 1 to 3 condensed rings, $R_2$ is hydrogen or a saturated or unsaturated aliphatic group containing up to 30 carbon atoms and n is at least 1 with carbon monoxide at a temperature of about 60° to 300° C. and a pressure of about 1 to 700 atmospheres in the presence of about 0.01 to 15%, based on the total weight of aromatic amine present, of a copper halide catalyst, oxygen in an amount less than the minimum amount which will form an explosive mixture of carbon monoxide and oxygen, a saturated aliphatic alcohol having up to 6 carbon atoms and an organic dehydrating agent selected from the group consisting of orthoesters, ketals, acetals, enolethers and trialkylorthoborates, said dehydrating agent being present in an amount sufficient to remove water formed during said reaction and the reaction being carried out in the presence of a stoichiometric excess of amine relative to the amount of alcohol present in the reaction zone.

13. The process of claim 12 wherein the copper halide catalyst is copper(II) chloride or copper(II) bromide and it is present in an amount of about 0.1 to 5%, based on the total weight of aromatic amine present.

14. The process of claim 12 wherein said dehydrating agent is an orthoester whose ester moieties have up to 6 carbon atoms.

15. The process of claim 12 wherein said aromatic amine is a mononuclear aromatic amine.

* * * * *